United States Patent [19]
Benja-Athon

[11] Patent Number: 5,843,052
[45] Date of Patent: Dec. 1, 1998

[54] IRRIGATION KIT FOR APPLICATION OF FLUIDS AND CHEMICALS FOR CLEANSING AND STERILIZING WOUNDS

[76] Inventor: Anuthep Benja-Athon, 210 E. 36th St., New York, N.Y. 10016

[21] Appl. No.: 727,701

[22] Filed: Oct. 4, 1996

[51] Int. Cl.$^6$ .................................................. A61M 35/00
[52] U.S. Cl. ........................................... 604/289; 604/293
[58] Field of Search .................................... 604/289, 290, 604/293, 310, 311, 313

[56] References Cited

U.S. PATENT DOCUMENTS

| | | | |
|---|---|---|---|
| 2,938,495 | 5/1960 | Hinton | 604/289 |
| 3,574,239 | 4/1971 | Sollerud | 604/289 |
| 4,679,551 | 7/1987 | Anthony | 604/289 |
| 4,850,997 | 7/1989 | DuBose | 604/289 |
| 4,892,526 | 1/1990 | Reese | 604/310 |
| 5,312,385 | 5/1994 | Greco | 604/289 |
| 5,447,504 | 9/1995 | Baker et al. | 604/289 |

*Primary Examiner*—Robert A. Clarke
*Assistant Examiner*—David J. Cho

[57] ABSTRACT

An irrigation tubing kit adaptable to reversibly attach to a faucet, a hose or a tubing comprises a flexible conduit having at one end of the conduit a coupling member in continuity with a filter member in continuity with a flow-regulating valve with variably adjustable aperture and dial, a semi-rigid tubing extension member for admission of chemicals and medications which is regulated by another flow-regulating valve with variably adjustable aperture and dial, a semi-rigid bypass port extension member, a disperser member at the end of the conduit, and a separate reservoir means of storing chemicals and medications adaptable to reversibly attach to the semi-rigid tubing extension member for the delivery of chemicals and medications into the conduit of the irrigation tubing kit. The flowing fluid originates from a faucet, a hose or a tubing and directly flows into the conduit by successively passing through the coupling member, filter member and flow-regulating valve and provides the force to generate filtered fluid to remove foreign bodies and debris from and to dispense the chemicals and medications from the reservoir means directly into the conduit to sterilize the wound, ulcer, laceration, breakdown of the skin and mucosa of the body.

8 Claims, 1 Drawing Sheet

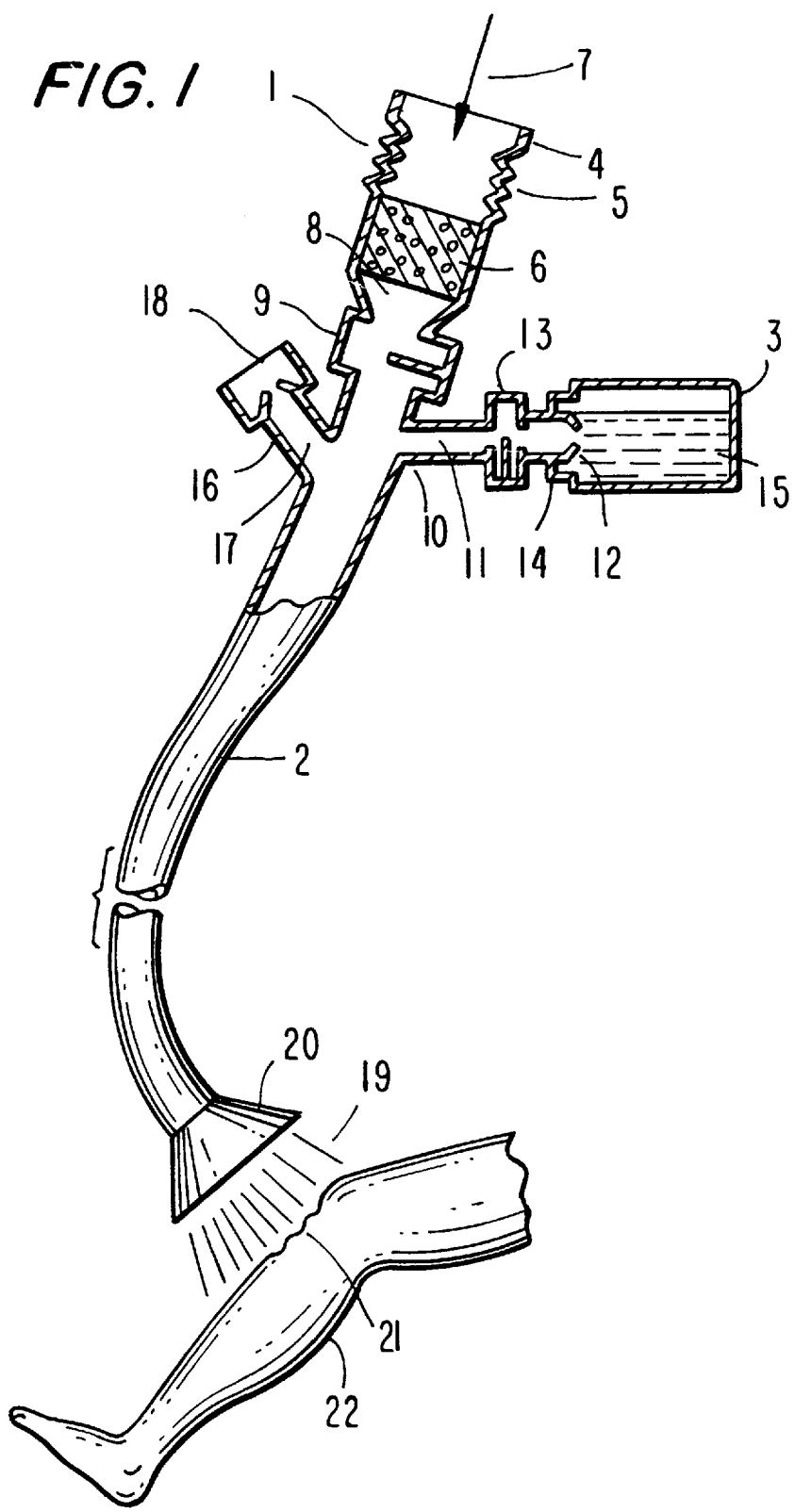

IRRIGATION KIT FOR APPLICATION OF FLUIDS AND CHEMICALS FOR CLEANSING AND STERILIZING WOUNDS

FIELD OF THE INVENTION

A compact irrigation tubing kit uses flowing water from a faucet or a hose and vials of chemicals and medications for optimal cleaning and debridement of wound in any settings and environments.

BACKGROUND OF THE INVENTION

The objective of the present invention is to cleanse, debride and sterilize wound, ulcer, laceration and breakdown of structures, such as but not limited to, skin, mucosa, and to irrigate cavities, organs and body parts of human and animal.

The objective of the present invention is to eliminate or reduce the infection of said structures, leading to morbidity and mortality.

The objective of the present invention is to eliminate or reduce the transmission of diseases, leading to morbidity and mortality.

The objective of the present invention is to eliminate or reduce the iatrogenic infection of said structures and to eliminate or reduce iatrogenic transmission of diseases, leading to morbidity and mortality.

The objective of the present invention reduces pain and suffering in the process of achieving said goals.

The objective of the present invention is to give means of effective cleansing, debriding, sterilizing said structures in any and all environments and settings.

The objective of the present invention is to give availability of irrigation of said structures in any and all environments and settings such as, but not limited to, in emergency room, clinic, home, hotel, outdoor, fields, outer space by astronaut, countries which lack or do not have proper or adequate facilities and means including health care facility.

The objective of the present invention is to reduce or eliminate the unsterile, unclean and unsanitary techniques in any and all said environments and settings in which anyone engages in said procedures on said structures to achieve said objectives.

The integrity of the skin, body lining, mucosa, covering of the body parts of human and animal ensures the survival and well-being of said organisms. The breach, breakdown, laceration, disintegration of said structures lead to pain and suffering, infection, morbidity and mortality.

Today, people are more mobile and are ever more present in different environments, settings, lands, countries, and space. People are exposed to structures and environments which potentially cause said damages to said structures. Furthermore, people are living longer and whose said structures are more prone to said disorders.

It is the observation of this physician patent applicator, whose extensive medical training including many years in surgery, that proper technique of cleaning, debriding, cleansing, sterilizing and caring of said body parts are unknown or poorly understood by most people including most health care providers.

Two critical factors in said management of said structures are the removal of foreign bodies, particles, nonviable and dead particles and debris, and the removal of toxic and waste from said structures. The irrigation of said structures with copious volume of clean water preferably with medication will achieve said goals. The strict adherence to proper technique of care of said structure is essential. As stated, these factors are lacking or deficient.

Lack of Equipment: In said settings and environments in America and other countries, there is neither effective, efficacious, nor readily available kit for cleaning, cleansing, debriding, removing foreign particles and live, nonviable and dead debris—both animate and inanimate— from the said structures. Often the said parts are not cleaned at all. Often said debris and particles are left in said structures of the patient.

In most American homes and away-from-homes, there is no said equipment for achieving said objectives. In any and all other said environments and settings, unavailability is the rule.

In medical settings and environments such as hospitals, clinics, and emergency rooms, at best, if said objectives are acknowledged by the health care providers, the washing process of said structure is improvised. Perhaps a small and inadequate volume of sterile fluid is poured onto said structures leaving said structure uncleaned. At best, if available or physically possible, said structures are immersed in water or saline solution in a basin which may not have been cleaned or sterile or is contaminated during the use. Furthermore, pain and suffering are inflicted on the patient when his/her said structure is put under running tap water in awkward manner and setting which are not meant to achieve the objective.

In intensive care units and wards of hospitals said improvision is a routine and often is inadequate.

Lack of Sterile Technique: Most people in America and throughout the world including health care providers in any and all settings and environments lack the correct and proper skill to clean, cleanse, debride damaged structure of the body as described.

The lack of proper equipment and its availability, and the knowledge by most people in any and all said settings and environments cause pain, suffering, infection, transmission of diseases, morbidity and mortality.

The present invention eliminates said problems.

SUMMARY OF THE INVENTION

Almost all people in America and throughout the world including health care providers in all settings and environments lack the proper equipment and correct and proper skill to clean, cleanse and debride damaged structure such as wound, ulcer, and laceration of the body. The lack of proper equipment and its availability, and the knowledge by most people cause pain, suffering, infection, transmission of diseases, morbidity and mortality.

To overcome the aforementioned setbacks, the present invention provides a compact yet totally effective irrigation and sterilization kit to effectively clean, cleanse and debride damaged structure such as wound, ulcer, laceration, breakdown of the skin and mucosa of the body in any and all settings and environments including in outer space. Essentially, an irrigation tubing kit comprises a flexible conduit having at one end of the conduit a coupling member adaptable to reversibly attach said tubing kit to a faucet, a hose or a tubing in a setting such as a bathroom, in a field in a remote area and in a clinic. In continuity with said coupling means is a filter member of said conduit to sequester and eliminate living organisms and impurity particles from the flowing fluid from said faucet, hose or tubing. In continuity with said filter means is a flow-regulating valve with variably adjustable aperture and dial to regulate the volume of the filter fluid flowing in said conduit. On one side of said tubing kit is a short semi-rigid tubing extension member with a short conduit in continuity with said conduit and an opening adaptable to couple to a separate vial of chemicals and medications and to admit said chemicals and medications into said conduit. The flow of said chemicals and medications is regulated by another flow-regulating valve with variably adjustable aperture and dial. On another side of said tubing kit is a short semi-rigid bypass port extension member with a short conduit in continuity with the conduit of said tubing kit and an opening adaptable to introduce fluids and chemical substances into the conduit of said tubing kit beyond said filter member. A disperser member at the end of the conduit to distribute said chemical, medications and fluid over the wound, ulcer, laceration, breakdown of the skin and mucosa of the body. A separate component of said tubing kit is said reservoir means such as said vial which stores chemicals and medications prior to the application of said tubing kit and is adaptable to deliver said chemicals and medications into the conduit of the tubing kit. The flowing fluid from a faucet, hose or tubing successively flows through the coupling member, filter member and flow-regulating valve provides the force to generate filtered fluid to remove foreign bodies and debris from and to dispense the chemicals and medications from the reservoir directly into the conduit to sterilize the wound, ulcer, laceration, breakdown of the skin and mucosa of the body.

BRIEF DESCRIPTION OF THE DRAWING

FIG. 1 is a schematic view of the present invention.

DESCRIPTION OF THE PREFERRED EMBODIMENTS

FIG. 1 shows the compact and open-system irrigation tubing kit 1 of the present invention. It is obvious from this illustration of the preferred embodiment that tubing kit 1 fulfills the aforementioned objectives of providing a totally effective irrigation means of cleaning, cleansing and debriding bodily structures such as wound, ulcer, laceration, breakdown of the skin and mucosa of the body of a person in any and all environments and settings such as emergency room, clinic, home, hotel, outdoor, field, outer space by astronaut, countries where there is a lack of proper or adequate facilities and means including health care facility.

FIG. 1 shows irrigation tubing kit 1 comprises a conduit or tubing 2 and a reservoir means 3 such as, but not limited to, a reversibly sealed vial 3 adaptable to be separate (not shown in the figure) during storage from conduit 2 prior to the application of reservoir means 3 and the dispensation of stored chemical and medications 15 in vial 3 to tubing kit 1.

As shown in the figure, at one end of tubing kit 1 is the enlarged part 4 of conduit 2 and the coupling means 5 adaptable to reversibly securely connect and attach entire tubing kit 1 to a faucet, a hose or a tubing (not shown) which provides flowing fluid 7 represents by a straight single arrow such as, but not limited to, water in any and all settings and environments such as a bathroom, in a field in a remote area and in a clinic. The potential, hydrostatic and kinetic energies of flowing fluid 7 cause the unidirectional flow of fluid 7 into conduit 2 from said faucet, hose or tubing. Flowing fluid 7 directly enters conduit 2 from said faucet, hose or tubing into conduit 2 at coupling means 5 and successively passes through enlarged part 4, coupling means 5, filter means 6. Filter means 6 is adaptable to be an integral part of conduit 2. On the other hand, filter means 6 can be reversibly connected or engaged to conduit 2 and, therefore, can be removed from conduit 2. In both circumstances, filter means 6 eliminates and sequesters living organisms and impurity particles which are present in fluid 7 flowing through filter means 6 and produces filtered fluid 8 which is free from said organisms and particles. In continuity, conduit 2 also comprises a flow-regulating valve 9 beyond filter means 6 with variably adjustable aperture and dial to regulate the volume of filter fluid 8 flowing in conduit 2.

Beyond flow-regulating valve 9 on one side of conduit 2 is a short semi-rigid tubing extension member 10 with short conduit 11 in continuity with conduit 2 and an opening 12 adaptable to couple to reservoir means 3 at opening 14 to admit chemicals and medications stored in reservoir means 3 into conduit 2.

As stated above, irrigation tubing kit 1 comprises said reservoir means 3 such as, but not limited to, sealed vials each of which has a reversibly closed opening 14. Prior to the use of irrigation tubing kit 1, reservoir means 3 stores chemicals and medications 15 such as, but not limited to, local anesthetics, sterilizing medications, antiseptics, disinfectants, antibodies, chelating agents, opening 14 is sealed and said vial is kept in storage separate from conduit 2. Reservoir means 3 can contain various chemical and medication or various mixture of chemicals and medications. When the application of irrigation tubing kit 1 is called for, reservoir means 3 is adaptable to be reversibly attached and connected to tubing kit 1 at the opening 14 which is adaptable to reversibly attach and connect to opening 12 of tubing extension member 10 to deliver chemicals and medications 15 into conduit 11 and then into conduit 2. The flow of chemicals and medications 15 is regulated by another flow-regulating valve 13 with variably adjustable aperture and dial on short semi-rigid tubing extension member 10. In other words, when reservoir means 3 is connected to short semi-rigid tubing extension member 10, the cavity of the vial is in continuity with conduit 11 and conduit 2 via opening 14, opening 12 of conduit 11, valve 13 and conduit 2. The aforementioned potential, hydrostatic and kinetic energies of fluid 7 cause the unidirectional flow and, therefore, dispensation of chemicals and medications 15 from reservoir means 3 directly into conduit 11 and then into and through beyond conduit 2. The mix of flowing filtered fluid 8 in conduit 2 with chemicals and medications 15 becomes flowing fluid 19 which ultimately cleans, cleanses and sterilizes wound, ulcer, laceration, breakdown of the skin and mucosa 21 of the body part 22 such as the leg.

On one side of said tubing kit 1 is another short semi-rigid bypass port extension member 16 such as a port comprises conduit 17 in continuity with conduit 2 and an opening 18 adaptable for the introduction of other types of fluids and chemical substances directly into conduit 17 and conduit 2 beyond filter member 9.

A disperser member 20 of tubing kit 2 at the end of conduit 2 disperses and distributes flowing fluid 19 which comprises of chemicals and medications 15 in flowing fluid 8 on wound, ulcer, laceration, breakdown of the skin and mucosa 21 of the body part 22. Disperser member 20 is the enlarged member of the end of conduit.2 and comprises of a diffuser which regulates the force, pressure, and volume of flow per unit time of flowing fluid 19.

Although various preferred embodiments of this invention have been described, it will be appreciated by those skilled in the art that variations may be made without departing from the spirit of the invention or the scope of the aforementioned claims.

Although the use of the present invention is for wounds, ulcers, lacerations and breakdown of skin and mucosa of humans and animals, it will be appreciated that the present invention can be used with other organs and body parts within the scope and spirit of the present invention.

Although the use of the present invention is in humans and animals, it will be appreciated that the present invention can be used with living and inanimate objects within the scope and spirit of the present invention.

I claim:

1. A compact and open-system irrigation tubing kit comprises a flexible conduit having at one end of said conduit a filter member in continuity with a coupling member adaptable to reversibly attach said tubing kit to a faucet, a hose and a tubing in a bathroom, a field in a remote area, a clinic and outer space wherein the unidirectional flow of fluid from said faucet, hose and tubing directly into said conduit and the unidirectional flow of medications and chemicals directly into said conduit from a reservoir means adaptable to reversibly attach to a semi-rigid tubing extension member of said tubing kit beyond said filter member to the wound, ulcer, laceration, breakdown of the skin and mucosa is caused by the potential, hydrostatic and kinetic energies of said flowing fluid for the removal of foreign bodies and debris and the sterilization of said wound, ulcer, laceration, breakdown of the skin and mucosa of the body comprising:

said coupling member adaptable to reversibly connect said tubing kit to said faucet supplying said fluid;

said coupling member adaptable to reversibly connect said tubing kit to said hose supplying said fluid;

said coupling member adaptable to reversibly connect said tubing kit to said tubing supplying said fluid;

said filter member for eliminating and sequestering living organisms and impurity particles from said flowing fluid adaptable to reversibly attach to said coupling member;

flow-regulating valve member for regulating said flow of the filtered fluid;

said semi-rigid tubing extension member for coupling said reservoir means to said tubing kit;

separate reservoir means of storing chemicals and medications adaptable to reversibly attach to said semi-rigid tubing extension member;

flow-regulating valve means of regulating the dispensation of said chemicals and medications from said reservoir means;

semi-rigid bypass port extension member of said tubing kit; and disperser member at the end of said conduit.

2. The irrigation tubing kit according to claim 1 wherein said filter member for eliminating and sequestering living organisms and impurity particles from said flowing fluid adaptable to reversibly attach to said coupling member is a filter means of segregating living organisms and impurity particles from said fluid.

3. The irrigation tubing kit according to claim 1 wherein said flow-regulating valve member for regulating said flow of the filtered fluid is a valve means with adjustable aperture.

4. The irrigation tubing kit according to claim 1 wherein said semi-rigid tubing extension member for coupling said reservoir means to said tubing kit is a short side conduit extension of said conduit of said tubing kit comprises a short conduit in continuity with the conduit of said tubing kit and an opening means of said short conduit adaptable to reversibly couple with said reservoir means and to admit said chemicals and medications from said reservoir means.

5. The irrigation tubing kit according to claim 1 wherein said reservoir means of storing chemicals and medications adaptable to reversibly attach to said semi-rigid tubing extension member is a sealed vial comprises a reversibly closed opening adaptable to reversibly couple to said opening means of said short conduit.

6. The irrigation tubing kit according to claim 1 wherein said flow-regulating valve means of regulating the dispensation of said chemicals and medications from said reservoir means is a valve means with adjustable aperture on said semi-rigid tubing extension member of said conduit.

7. The irrigation tubing kit according to claim 1 wherein said semi-rigid bypass port extension member of said tubing kit is a short side extension of said tubing kit beyond said filter member comprises a short conduit in continuity with said conduit of said tubing kit and an opening adaptable to introduce fluids and chemical substances into the conduit of said tubing kit.

8. The irrigation tubing kit according to claim 1 wherein said disperser member at the end of said conduit is the enlarged member of the end of said conduit.

* * * * *